United States Patent [19]
Elliot et al.

[11] Patent Number: 5,660,603
[45] Date of Patent: Aug. 26, 1997

[54] PROCESS FOR SEPARATING SELECTED COMPONENTS FROM MULTI-COMPONENT NATURAL GAS STREAMS

[75] Inventors: Douglas G. Elliot, Houston; Jong J. Chen, Sugarland, both of Tex.

[73] Assignee: International Process Services, Inc., Houston, Tex.

[21] Appl. No.: 523,719

[22] Filed: Sep. 5, 1995

[51] Int. Cl.$^6$ ..................................................... C01B 3/32
[52] U.S. Cl. ........................... 48/127.5; 48/127.3; 48/190; 62/632; 585/15
[58] Field of Search ..................... 48/127.3, 127.5, 48/190; 423/220; 585/15; 62/632, 633, 929

[56] References Cited

U.S. PATENT DOCUMENTS

| | | | |
|---|---|---|---|
| 1,962,525 | 6/1934 | Richardson | 423/220 |
| 2,097,454 | 11/1937 | Fischer | 423/220 |
| 2,271,214 | 1/1942 | Welty, Jr. | 48/127.3 |
| 2,356,407 | 8/1944 | Hutchinson | 48/190 |
| 2,363,529 | 11/1944 | Hutchinson | 585/15 |
| 2,375,559 | 5/1945 | Hutchinson et al. | 423/220 |
| 2,375,560 | 5/1945 | Hutchinson et al. | 423/220 |
| 2,399,723 | 5/1946 | Crowther | 585/15 |
| 3,456,028 | 7/1969 | Gerhold et al. | 260/674 |
| 4,044,100 | 8/1977 | McElroy, Jr. | 423/226 |
| 4,112,050 | 9/1978 | Sartori et al. | 423/223 |
| 4,370,156 | 1/1983 | Goddin et al. | 62/17 |
| 4,409,102 | 10/1983 | Tanner | 210/603 |
| 4,934,153 | 6/1990 | Ebinuma et al. | 62/66 |
| 5,044,164 | 9/1991 | Bee | 62/46 |
| 5,304,356 | 4/1994 | Iijima et al. | 422/226 |
| 5,344,627 | 9/1994 | Fujii et al. | 423/220 |
| 5,362,467 | 11/1994 | Sakai et al. | 423/223 |
| 5,364,611 | 11/1994 | Iijima et al. | 423/220 |
| 5,397,553 | 3/1995 | Spencer | 48/190 |
| 5,405,595 | 4/1995 | Tomikawa et al. | 423/220 |
| 5,473,904 | 12/1995 | Guo et al. | 585/15 |

FOREIGN PATENT DOCUMENTS

| | | | |
|---|---|---|---|
| 610237 | 12/1960 | Canada | 48/190 |
| 0031432 | 3/1981 | Japan | 423/220 |
| 3-250081 | 7/1991 | Japan | 423/220 |
| 3-364198 | 10/1991 | Japan | 423/220 |
| 4141217 | 5/1992 | Japan | 423/220 |
| 538429 | 2/1993 | Japan | 423/220 |
| 5146637 | 6/1993 | Japan | 423/220 |
| 568290 | 3/1945 | United Kingdom | 585/15 |

OTHER PUBLICATIONS

Hezog et al, "Feasability . . . In the Deep Ocean", Environmental Progress (vol. 10, No. 1) 1991.
Baes et al, "Options for the Collection and Disposal of Carbon Dioxide", May 1980.
Baes et al "The Collection, Disposal and Storage of Carbon Dioxide", 1980.
Engless, "Clathrate Hydrates"; ACS, 1993.
E. P. Sloan, "Natural Gas Hydrate . . . Art", Reue de l'Institute, Francais Du Petrole, 1990.
Wilcox et al, "Natural Gas Hydrates", IOE Chem., vol. 33, No. 5 Sep. 1939.
Riki Kobayashi, Principle Investigator; Solid Deposition in Hydrocarbon Systems—Hydrates of Natural Gases; Jan. 1, 1990–Dec. 31, 1994.
L. Kohl & Fred C. Riesenfeld; Gas Purification Fourth Edition; pp. 247–297.

(List continued on next page.)

*Primary Examiner*—Timothy McMahon
*Attorney, Agent, or Firm*—Pravel, Hewitt, Kimball & Krieger

[57] ABSTRACT

A process for separating components of gas mixtures which have different hydrate forming characteristics which uses an aqueous liquid to absorb one of the gases preferentially by attaining conditions slightly above the catastrophic point at which gas hydrates form. Specifically, the separation of gas mixtures containing light hydrocarbons and carbon dioxide is accomplished without significantly reducing the pressure of the carbon dioxide or without requiring significant amounts of heat energy for regeneration.

17 Claims, 2 Drawing Sheets

OTHER PUBLICATIONS

John Happel, et al.; A Novel Apparatus; The Study of Separation of Nitrogen From Methan by Hydrate Formation Using a Novel Apparatus; pp. 412–424.

R. Kobayashi, et al.;Solubility Measurements of Methane and Ethane in Water at Hydrate Conditions; Sep., 1995.

Gary K. Jacobs and Derrill M. Kerrick; Methane: An Equation of State with Application to the Ternary System $H_2O$—$CO_2$—$CH_4$; Sep. 4, 1980; pp. 607–614.

John A. Nlghswande; Journal of Chemical and Engineering Data; 1989; Solubilities of Carbon Dioxide in Water and 1 Wt % NaCl Solution at Pressures Up to 10 Mpa and Temperatures from 80 to 200C; pp. 355–360.

Sanggono Adisasmlto; Journal of Chemical and Engineering Data; 1991; Hydrates of Carbon Dioxide and Methane Mixtures; pp. 68–71.

Kazunari Ohgaki; Journal of Chemical Engineering of Japan; 1993; Formation of $CO_2$ Hydrate in Pure and Sea Waters; pp. 558–564.

PROCESS FOR SEPARATING SELECTED COMPONENTS FROM MULTI-COMPONENT NATURAL GAS STREAMS

FIELD OF THE INVENTION

This invention relates to a process for separating components of gas mixtures and, more particularly, to a separation process utilizing differences in hydrate formation characteristics to separate components of gas mixtures which contain light hydrocarbons.

BACKGROUND OF THE INVENTION

Natural gas reservoirs frequently contain carbon dioxide. Some reservoirs around the world may contain up to about 90% carbon dioxide. Generally, this carbon dioxide must be separated from the natural gas stream because it contains no thermal heating value and it does have acidic properties which can corrode natural gas equipment.

There are numerous methods available for removing carbon dioxide from natural gas streams. Most commonly used is a chemical absorption process wherein a chemical solvent such as ethanolamine is used to selectively and chemically bind the carbon dioxide for removal. This occurs by passing the unpurified natural gas stream through a packed or trayed tower in which the chemical solvent is flowing countercurrently to the natural gas stream.

The chemical solvent will bind and remove the carbon dioxide and a purified natural gas stream emerges from the top of the tower. The chemical solvent then rich in carbon dioxide must be regenerated so that the solvent can be reused or recycled. This typically occurs by lowering the pressure and raising the temperature of the carbon dioxide rich solvent stream in a regeneration tower. This tower generally consists of a reboiler and a reflux condensing system. Heat is added in the reboiler to break the carbon dioxide-solvent bonds and the reflux system condenses any solvent vapors that might escape with the carbon dioxide gas. The purified carbon dioxide emerges from the top of the tower at a pressure substantially lower than the original natural gas stream.

There are two problems with this type of separation system. First, the regeneration process requires considerable energy for heating. There are physical absorption processes available which require less heating for regeneration, however, these process are generally less selective.

Second, the carbon dioxide that emerges from the regeneration tower is at a low pressure. The low pressure carbon dioxide coming from the conventional regenerator often requires additional costs and equipment for recompression in order to inject the carbon dioxide back into the reservoir; a requirement that has become more important due to environmental concerns over "green house" gases such as carbon dioxide. Traditional venting of carbon dioxide in significant amounts to the atmosphere is no longer environmentally acceptable in some parts of the world.

It would be desirable to have a process which effectively separates carbon dioxide from natural gas but requires lower energy consumption and does not significantly lower the pressure on the carbon dioxide removed from the gas stream in the solvent regeneration step.

Another naturally occurring phenomenon associated with natural gas systems is the formation of gas hydrates. Gas hydrates are solids which are formed by a physical reaction between water and low molecular gases such as methane and carbon dioxide. On a molecular level, gas hydrates appear to resemble a class of compounds known as clatharates. Water molecules assemble into cage-like structures with cavities of a specific size trapping hydrate forming gases inside.

A significant amount of experimentation has been done on hydrate formation to address the problems caused by solids buildup in pipelines and processing equipment, particularly in colder environments. It has been determined that hydrate forming compounds have different hydrate forming characteristics. The catastrophic point, that point at which solid hydrate formation begins, is a function of temperature, pressure, and gas composition. This variation in hydrate formation characteristics makes possible a separation process which could selectively remove hydrate forming compounds. However, because gas hydrates are solids, process equipment would have to be able to deal with multi-phase fluids and the problems associated with solids accumulation.

Prior studies of hydrate formation in pure component gases have shown that a significant amount of pre-solid hydrate structures exist in water even when the temperature is several degrees above the point where solid hydrates normally form. These prior pure component gas hydrate experiments have also shown that some gas is retained in the water phase by these pre-solid hydrate formations. The mechanism by which these pre-solid hydrate structures retain gases is not clear. However, hereinafter that mechanism will be referred to as absorption.

Scrubbing natural gas with water to remove some of the impurities contained therein has been known in the art for many years. However, the enhanced absorption which occurs as a result of the formation of pre-solid hydrates and the selectivity at which such absorption occurs has not been known or utilized. The term "selectivity" as used herein means the difference in the amount of one gas absorbed relative to another gas in the same mixture.

It is an object of this invention to provide a separation process which utilizes differences in gas absorption caused by pre-solid hydrate formation characteristics. More specifically, it is an object of this invention to utilize selectivity differences in pre-solid hydrate absorption between carbon dioxide and light hydrocarbon gases to provide a separation system. The term "light hydrocarbon" as used herein generally includes, but is not limited to, any one or more of methane, ethane, propane, and/or natural gas. "Natural gas" is a mixture of two or more of such hydrocarbon gases. Further, it is an object of this invention to provide such a separation system that does not significantly reduce the carbon dioxide pressure or require large energy inputs for regeneration.

SUMMARY OF THE INVENTION

The present invention provides a process for separating components of gas mixtures which have different pre-solid hydrate forming characteristics. The invention uses an aqueous liquid to selectively absorb one of the gases preferentially to the other gases in the mixture by attaining conditions under which pre-solid hydrates form in the water. These pre-solid hydrate structures selectively trap different hydrate forming gases. This selective absorption makes the separation process of this invention possible.

When applied specifically to the separation of carbon dioxide from natural gas streams, the invention accomplishes the removal of carbon dioxide without significantly reducing the pressure of the carbon dioxide, and/or without requiring significant amounts of energy for solvent regeneration and circulation.

DETAILED DESCRIPTION OF INVENTION

This invention will typically be used to separate out impurities from light hydrocarbon gas streams. Particularly, the process of the present invention can be utilized to remove carbon dioxide from light hydrocarbon streams containing about 4 to about 90% carbon dioxide. The embodiments of the invention shown in FIG. 1 and FIG. 2 demonstrate separation processes for a gas mixture containing carbon dioxide and light hydrocarbons using an aqueous liquid. The term "aqueous liquid" as used herein means water or sea water alone, or with additives such as sodium chloride. As used herein, "sea water" refers to water from the sea which typically contains three to seven percent by weight sodium chloride. This invention may also be used for separation of other gas mixtures containing hydrate forming compounds.

The invention primarily consists of a process for contacting the gas stream with an aqueous liquid while the temperature and pressure are controlled to attain conditions around which pre-solid hydrates form in the liquid stream. The pre-solid hydrates selectively absorb different hydrate forming gases effectively separating the components of the gas feed stream.

The catastrophic temperature is the temperature at which solid hydrates form at a given pressure. The catastrophic temperature for hydrate formation will change with several variables including pressure, composition of the gas, and composition of the liquid. Because the catastrophic temperature varies with pressure and composition, the catastrophic temperature must be determined for each application of the invention from data that is generally available. See for example, Clathrate Hydrates of Natural Gases by E. Dendy Sloan, Jr. published by Marcel Dekker, Inc., New York, N.Y., 1990.

Figure 1:
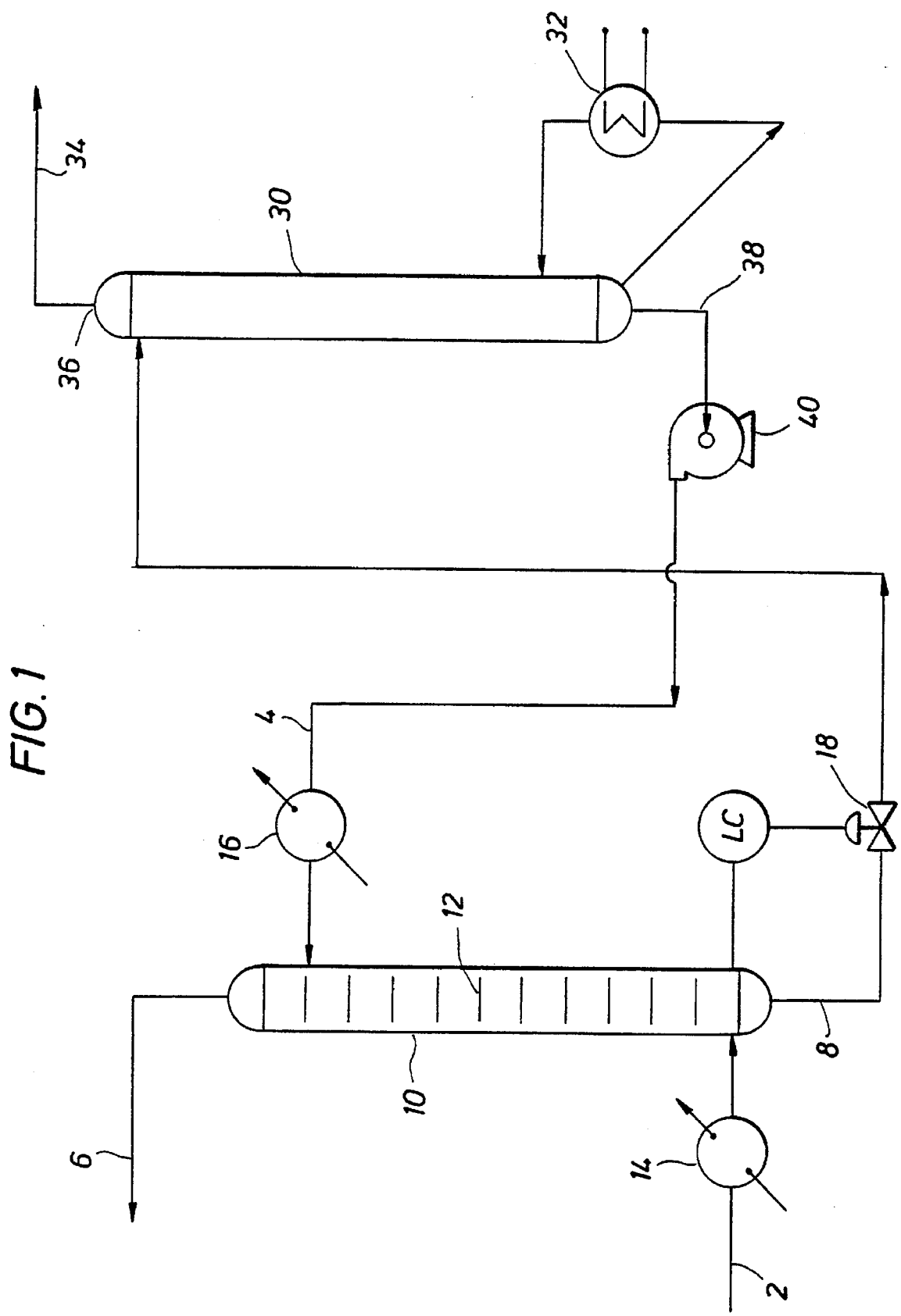
FIG. 1 is a process flow diagram of an embodiment of the process used to separate carbon dioxide from a light hydrocarbon gas stream.

The invention is best understood with reference to FIG. 1 which illustrates an embodiment of the invention in a schematic flow diagram. This embodiment features two main vessels, a high pressure absorbing column 10 and a high pressure regeneration column 30.

In the high pressure absorbing column 10, the gas feed stream 2 is contacted with the aqueous liquid stream 4. The temperature and pressure in the high pressure absorbing column 10 are controlled to attain conditions around which pre-solid hydrates form in the liquid phase.

The liquid feed stream 4 used to absorb carbon dioxide gas will typically be water or sea water. To enhance the absorption of carbon dioxide by the pre-solid hydrate formations in the aqueous liquid it can be advantageous to use certain hydrate inhibitors or surfactants along with the water. These additives lower the temperature at which hydrate formation occurs. They also selectively inhibit the formation and growth of methane hydrate crystals, a competitive reaction to carbon dioxide hydrate formation.

One hydrate inhibitor which has worked well with the water is sodium chloride. Experimental data using concentrations from 0.0% to 18.0% percent by weight of sodium chloride in water as the absorbing solution showed carbon dioxide separation improves with the addition of sodium chloride. The optimum concentration of the sodium chloride in the solution was between 4.0 and 8.0 percent. TABLE 1 shows these experimental results.

TABLE 1

Preliminary Results from Constant Pressure Hydrate Ramping Experiments for a Gaseous Mixture of $CO_2$ and $CH_4$ with an Inhibitor Solution.

| Experiment Type (Date) | Temperature analyzed, T(°C.) | Volume of Gas Added, cc | Methane Mole Fraction in Gas Phase, $Yc_1$ | Catastrophic Temperature, and Pressure Tc(°C.), (Psia) |
|---|---|---|---|---|
| Pure Water | 18.0 | 0.0 | 0.76 | 4.5, (521) |
| | 15.0 | 5.21 | 0.79 | |
| | 5.1 | 21.7 | 0.83 | |
| | 4.0 | 28.68 | 0.85 | |
| | 3.0 | 32.3 | 0.86 | |
| 2.0 Wt % Salt NaCl | 18.0 | 0.0 | 0.76 | 2.7, (521) |
| | 15.0 | 5.0 | 0.825 | |
| | 9.0 | 14.0 | 0.85 | |
| | 3.5 | 24.0 | 0.91 | |
| | 0.5 | 38.0 | 0.91 | |
| 4.0 Wt % Salt NaCl | 18.0 | 0.0 | 0.76 | 2.6, (521) |
| | 15.0 | 5.0 | 0.83 | |
| | 10.0 | 12.5 | 0.88 | |
| | 3.3 | 23.5 | 0.94 | |
| 8.0 Wt % Salt NaCl | 18.0 | 0.0 | 0.76 | 2.0, (521) |
| | 15.0 | 5.0 | 0.83 | |
| | 10.0 | 12.0 | 0.89 | |
| | 5.0 | 19.6 | 0.92 | |
| | 3.3 | 22.5 | 0.94 | |
| 18 Wt % Salt NaCl | 18.0 | 0.0 | 0.76 | 4.0, (521) |
| | 0.3 | 26.5 | 0.76 | |
| | −3.4 | 32.5 | 0.75 | |

This table also demonstrates that the aqueous liquid used as the absorbing liquid may be sea water. Using sea water as the aqueous liquid allows the invention to be more easily used in offshore applications where natural gas fields with high carbon dioxide content are commonly found.

It is believed that other water soluble salts may also be used in this invention.

The pressure to be maintained in the high pressure absorber column 10 can vary with the pressure of the available gas feed stream 2. This pressure will typically be between 500 and 1500 psig for gas feed streams 2 which come directly from gas production facilities. It is desirable to use a process pressure as high as possible to reduce the need for later recompression of the carbon dioxide stream 34.

The temperature in the high pressure absorption column should be controlled at the point where pre-solid hydrate structures form, typically within about 20° C. of the catastrophic temperature for carbon dioxide hydrates. Based on the experiments used to generate TABLE 1, successful operation would occur between about 1° C. and about 12° C. above the catastrophic temperature and the optimum being between about 2° C. and about 6° C. above the catastrophic temperature.

The temperature in the high pressure absorption column 10 will typically be controlled by cooling the gas feed stream 2 with a gas feed refrigeration chiller 14 and by cooling the liquid feed stream 4 with a liquid feed refrigeration chiller 16. Alternative temperature control systems are possible including energy recovery systems.

The high pressure absorbing column 10 contains trays 12 to enhance contact between the feed gas 2 and the aqueous liquid 4. Alternatively, the column may contain a packing medium or other means of enhancing gas-liquid contact.

The bottoms stream 8 from the high pressure absorbing column 10 contains the pre-solid hydrate structures which have selectively absorbed the carbon dioxide molecules. The purified light hydrocarbon stream 6 exits the column as a gas above the trays 12.

The bottoms stream 8 can be regenerated to remove or recover the absorbed carbon dioxide. This recovery may be accomplished by the addition of heat to the bottoms stream 8 and/or by a reduction in pressure on the bottoms stream 8 either of which will cause the pre-solid hydrate structures to decompose and thereby release the carbon dioxide molecules trapped inside.

The regeneration system shown in the embodiment of FIG. 1 uses the addition of heat along with a slight pressure reduction as the means of regeneration. The bottoms stream 8 is fed into a high pressure regeneration column 30. The pressure on the high pressure regeneration column 30 is maintained slightly below the pressure at which the high pressure absorbing column 10 is maintained. The pressure differential should be enough to push the bottoms stream 8 into the high pressure regeneration column 30 without requiring a mechanical pumping device.

Alternatively, the high pressure regeneration column 30 could be run at a pressure higher than the high pressure absorbing column 10. This alternative would require pumping the bottoms stream 8 into the high pressure regeneration column. An advantage of this alternative embodiment is that it allows total or partial condensing of the carbon dioxide rich exit stream 34.

The temperature on the high pressure regeneration column 30 is maintained above the formation point of the pre-solid hydrate structures. For example, if pre-solid hydrate structure formation occurred within 20° C. of the catastrophic temperature, the regeneration temperature would need to be greater than 20° C. This change in conditions causes the pre-solid hydrate structures to decompose.

Heat is added to the high pressure regeneration column 30 by means of a heat exchanger 32 on the bottom of the column. Other means of heating this column are acceptable.

The carbon dioxide rich exit stream 34 leaves the high pressure regeneration column 30 through a vent 36 at the top of the column. The regenerated liquid 38 is pumped from the bottom of the high pressure regeneration column 30 by means of a mechanical pump 40 and returned for use in the high pressure absorbing column 10.

Figure 2:
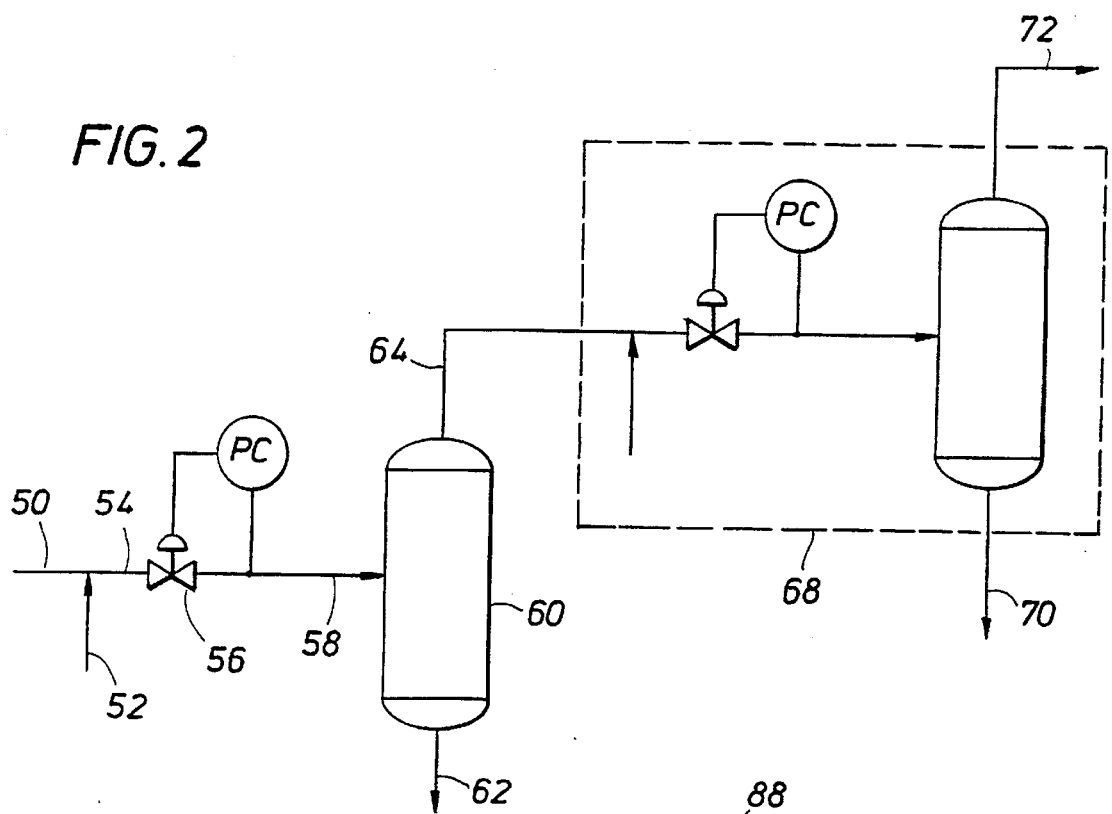
FIG. 2 is a process flow diagram of an alternative embodiment of the process used to separate carbon dioxide from a light hydrocarbon gas stream.

An alternative embodiment is shown in FIG. 2. In this embodiment a water stream 52 or water containing the additives previously discussed is injected into a high pressure feed stream 50. The combined stream 54 is then passed through an expansion valve 56 which reduces the pressure and thereby cools the gas stream. This expansion is controlled such that the associated temperature drop will approach the catastrophic temperature and pre-solid hydrate structures will be produced. Carbon dioxide will be selectively absorbed during this process.

After expansion, the combined stream 58 enters a liquid/gas separator vessel 60. The carbon dioxide rich water stream 62 falls to the bottom of the vessel where it can be removed. The remaining gas stream 64 flows out through the top of the liquid/gas separator vessel 60.

The remaining gas stream 64 may be subjected to additional stages 68 of this process until the percentage of carbon dioxide in the final exit gas stream 72 reaches the desired concentrations.

The carbon dioxide rich water streams 62 and 70 can be gathered and regenerated using the embodiment of the regeneration system shown in FIG. 1 or a similar regeneration embodiment.

Figure 3:
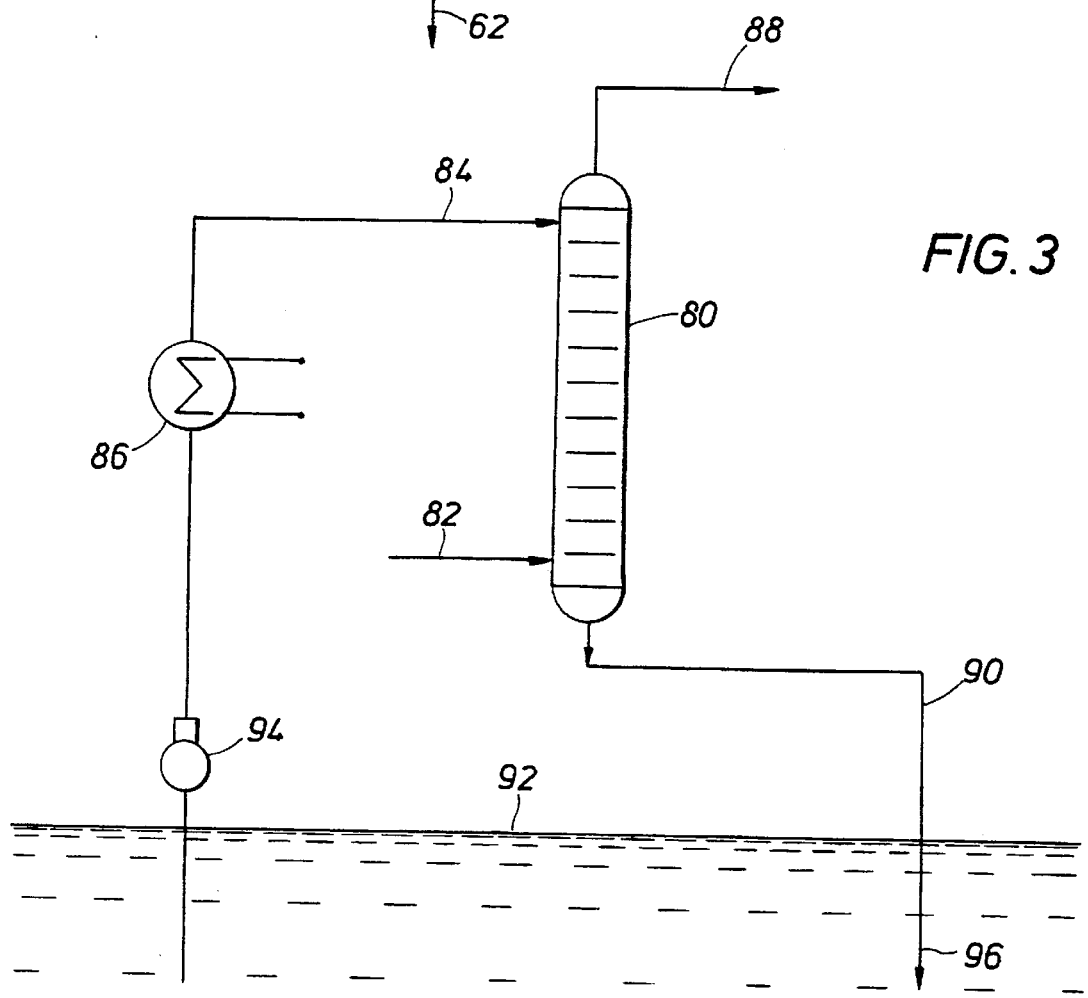
FIG. 3 is a process flow diagram of another alternative embodiment of the process used to separate carbon dioxide from a light hydrocarbon gas stream applicable to offshore operations.

Another alternative embodiment is shown in FIG. 3. This embodiment depicts a once through system for use preferably in offshore applications. This embodiment has a high pressure absorber 80 similar to the high pressure absorber 10 in FIG. 1.

The feed gas stream 82 flows into high pressure absorber 80 and is contacted by a sea water stream 84 flowing counter-currently in the high pressure absorber 80. The sea water stream 84 is cooled prior to entering the high pressure absorber by a cooling exchanger 86. The purified light hydrocarbon stream 88 emerges from the top of the high pressure absorber 80.

The bottoms stream 90 is discharged into the sea 92 by a pipe 96. When returned to an appropriate depth as described in U.S. Pat. No. 5,304,356, carbon dioxide hydrates will form which are stable and will remain in solid form at the bottom of the sea.

Having described the invention above, various modification of the techniques, procedures, material and equipment will be apparent to those in the art. In is intended that all such variations within the scope and spirit of the appended claims be embraced thereby.

What is claimed is:

1. A method of separating a mixture of gases, one of which is a hydrocarbon gas comprising:

contacting the mixture of gases with an aqueous liquid; and controlling the temperature and/or pressure during said contact such that the temperature of the liquid and gases during contact is slightly above the catastrophic temperature and within about 20° C. above the catastrophic temperature to selectively retain one or more of the gases.

2. The process of claim 1, wherein said aqueous liquid is water.

3. The process of claim 1, wherein said aqueous liquid is a sodium chloride solution.

4. The process of claim 1, wherein said aqueous liquid is sea water.

5. The process of claims 1, wherein said aqueous solution is water containing a water soluble salt.

6. The process of claim 1, wherein said hydrocarbon gas is methane.

7. The process of claim 1, wherein said hydrocarbon gas is ethane.

8. The process of claim 1, wherein said mixture of gases includes natural gas.

9. The process of claim 1, including:
regenerating said aqueous liquid, to release the gases selectively retained in the aqueous liquid.

10. The process of claim 9, wherein said aqueous liquid regeneration comprises regulating either the temperature or pressure of said aqueous liquid away from the catastrophic point for hydrate formation.

11. A method for removing carbon dioxide from a hydrocarbon gas stream containing about 4 to about 90% carbon dioxide, the process comprising:
contacting said carbon dioxide containing hydrocarbon gas stream with an aqueous solution comprising a water soluble salt in water up to the solubility limits; and
controlling the pressure and/or the temperature such that the temperature of the aqueous solution and gas stream during the contacting is slightly above the catastrophic temperature and within about 20° C. above the catastrophic temperature to selectively retain the carbon dioxide.

12. The process of claim 11, wherein said hydrocarbon gas is methane.

13. The process of claim 11, wherein said hydrocarbon gas is ethane.

14. A method of separating a mixture of gases, one of which is a hydrocarbon gas, comprising:
introducing an aqueous solution of water soluble salt and water into an absorption column;
introducing the mixture of gases into the absorption column;
controlling the temperature and pressure within said column such that the temperature is slightly above the catastrophic temperature and within about 20° C. above the catastrophic temperature to selectively retain one gas from the mixture of gases without forming solid hydrate structures; and
separating the aqueous solution and the selectively retained gas from the gases not retained whereby a substantial separation of at least one gas from the mixture of gases occurs.

15. The process of claim 14, wherein the mixture of gases comprises carbon dioxide and methane and the carbon dioxide is selectively retained.

16. The process of claim 14, wherein the temperature and pressure within said column is controlled such that the temperature is within about 12° C. above the catastrophic temperature.

17. The process of claim 14, wherein the temperature and pressure within said column is controlled such that the temperature is within about 6° C. above the catastrophic temperature.

* * * * *